United States Patent [19]

Calanchi

[11] Patent Number: 4,460,563

[45] Date of Patent: Jul. 17, 1984

[54] PROCESS FOR PREPARING MICROCAPSULES IN A LIQUID VEHICLE

[75] Inventor: Massimo Calanchi, Monza, Italy

[73] Assignee: Eurand S.p.A., Milan, Italy

[21] Appl. No.: 250,406

[22] Filed: Apr. 2, 1981

[30] Foreign Application Priority Data

Apr. 9, 1980 [IT] Italy ................... 21271 A/80

[51] Int. Cl.³ .............. B01J 13/02; B05D 7/00; B32B 9/02; A61K 9/62
[52] U.S. Cl. .................. 424/35; 427/213.32; 427/213.33; 428/402.24
[58] Field of Search .......... 252/316; 424/35; 427/213.32, 213.33; 428/402.24

[56] References Cited

U.S. PATENT DOCUMENTS

| | | | |
|---|---|---|---|
| 2,800,458 | 7/1957 | Green | 252/316 |
| 3,415,758 | 12/1968 | Powell et al. | 252/316 |
| 3,859,228 | 1/1975 | Morishita et al. | 427/213.36 |
| 3,891,570 | 6/1975 | Fukushima et al. | 427/213.36 |
| 3,897,361 | 7/1975 | Saeki et al. | 264/4.3 |
| 3,904,444 | 9/1975 | Anderson et al. | 428/402.24 |
| 3,937,798 | 2/1976 | Kitajima et al. | 423/659 |
| 3,943,063 | 3/1976 | Morishita et al. | 427/213.36 |
| 3,960,757 | 6/1976 | Morishita et al. | 427/213.36 |
| 4,102,806 | 7/1978 | Kondo et al. | 428/402.2 |
| 4,259,315 | 3/1981 | Lippman et al. | 424/37 |
| 4,293,677 | 10/1981 | Imai | 264/4 |
| 4,317,743 | 3/1982 | Chang | 428/402.21 |

FOREIGN PATENT DOCUMENTS

| | | |
|---|---|---|
| 1185155 | 1/1965 | Fed. Rep. of Germany . |
| 1542807 | 10/1968 | France . |
| 2267150 | 11/1975 | France . |
| 48-39620 | 6/1973 | Japan . |

OTHER PUBLICATIONS

Flinn, J. E. et al., Chemical Engineering, vol. 74, No. 25, pp. 171–173, (1967).

*Primary Examiner*—Benjamin R. Padgett
*Assistant Examiner*—M. Moskowitz
*Attorney, Agent, or Firm*—Gordon W. Hueschen

[57] ABSTRACT

The invention relates to a process for preparing microcapsules in a liquid vehicle, allowing to microencapsulate both water soluble and water insoluble substances, using either ionic or non-ionic systems, in which the membrane enclosing the core of the microcapsules is formed by a polymer selected from the group of the phthalates, and more particularly by hydroxypropylmethylcellulose phthalate.

16 Claims, No Drawings

PROCESS FOR PREPARING MICROCAPSULES IN A LIQUID VEHICLE

BACKGROUND OF THE INVENTION

The present invention relates to a process for preparing microcapsules in a liquid vehicle, in which the microcapsules consist of a core and a membrane enclosing it and have sizes which may be few microns as well as hundreds or thousands microns and generally are comprised in a broad granulometric range.

The present application is based on the chemical-physical phenomenon called coacervation. The term coacervation was introduced in the macromolecular chemistry by Kruyt and Bungenburg De Jong to describe the phenomenon of phase separation consisting of the formation of droplets of a polymer in a liquid form rather than solid aggregates, from a homogeneous solution of the polymer. This phase separated in the form of liquid and amorphous droplets is the coacervate.

When in the equilibrium liquid, particles insoluble or immiscible in it are dispersed, the coacervate covers said particles, this coating being fosteed by a decrease of the total free energy of the system. The present invention differs from the known systems of preparation of microcapsules, such as those disclosed in the U.S. Pat. Nos. 3,415,758, 2,800,457 and 2,800,458, because a membrane of hydroxy propylmethyl cellulose phthalate (HPMCP) is used, which is not disclosed in said prior art. With such a membrane it is possible to microencapsulate either water soluble substances or water insoluble substances, employing ionic as well as non-ionic systems, while with the systems described in the above mentioned patents, it is possible to microencapsulate only water insoluble substances with either ionic or non-ionic systems.

SUMMARY OF THE INVENTION

The microencapsulation process used in the present invention is carried out in a suitable vessel, under continuous stirring and may summarized in the following steps: (1) dissolution of the membrane forming polymer in a solvent which is the microencapsulation vehicle; (2) addition to said solution of the substance to be microencapsulated; (3) formation of coacervate by adding a suitable substance causing the phase separation and/or modifying a suitable chemical-physical variable of the system, such as pH, temperature, decreasing the solubility of the polymer in the vehicle; (4) deposition of coacervate, with formation of a continuous coating of polymer around the substance cores; (5) polymer setting; (6) eventual subsequent treatments.

This method of microencapsulation briefly consists of the deposition of a material adapted to form a wall around the particles forming the core of the microcapsules. For reasons of viscosity and volume ratios of the dispersed phase, the membrane forming polymer can deposit around the particles of the substance dispersed in the vehicle, and once deposited can remain in such a condition notwithstanding the system stirring. The deposit builds up quickly up to a maximum thickness which may be varied by changing the polymer/substance to be covered ratio, the degree and type of agitation, and this according to the protection degree one wants to obtain.

The microcapsules may be subjected to a supplementary treatment in order to harden the polymeric membrane, which may cause an improvement in stability and impermeability of the core in respect of the outer environment, in addition to other advantages. The hardening may be obtained by adding non solvents for the membrane or substances reacting with the membrane with or without the presence of catalysts, dehydrating substances or again by varying temperature or time of preparation. At last the obtainment of discrete microcapsules in dry form may be fostered by adding suitable substances acting as vehicle dehydratants or adsorbents.

DETAILED DESCRIPTION OF THE INVENTION

Membrane forming polymer

This invention is characterized, inter alia, by the fact that as a polymeric membrane hydroxypropylmethylcellulose phthalate is used, HPMCP is the shortened name for this substance which is available on the market from the Japanese company Shinetsu Chemical CO. under the two grades of HP 50 and HP 55, meaning that the pH value at which it is dissolved is 5.0 or 5.5.

Hydroxypropylmethylcellulose phthalate is obtained from hydroxypropylmethylcellulose (NF XIII) by esterification with phthalic anhydride. Its chemical structure is the following:

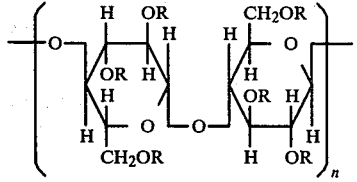

In the above formula R may be either a hydrogen atom or a methyl, hydroxypropyl, carboxybenzoyl, 2(2-carboxybenzoyl)propyl or acetyl group.

Such a polymer has a good stability at temperatures between $-3°$ C. and $+43°$ C., dry strength and light fastness and its physical properties are adapted for its use as a membrane. Solubility of HPMCP depends from pH, as known in literature and as shown by the following table of the tests conducted by applicant.

Dissolution time of HPMCP membranes at several pH values and as raw material at a temperature of 37° C. (25 cc of buffer solution in the DIFFUTEST ® analysis apparatus—Maximum control time 120 minutes).

| pH | HP 50 | HP 55 |
|---|---|---|
| 4.5 | >120 minutes | >120 minutes |
| 5.0 | 25 minutes | >120 minutes |
| 5.5 | 11 minutes | 90 minutes |
| 6.0 | 9 minutes | 30 minutes |
| 6.5 | 8 minutes | 28 minutes |

This property together with the non-toxicity of the polymer, allows its use in the pharmaceutical field as a pH-dependent membrane, in order to obtain a gastroresistant coating, i.e. insoluble at a gastric pH but soluble at an enteric pH. This use is only exemplary but not limiting, as HPMCP may be used in the pharmaceutical field for instance as a drug adsorption retardant, taste masking, and outer environment protecting membrane. It may also be used in the industrial fields for several different purposes.

Microencapsulation vehicle

As above indicated, the first microencapsulation step is the dissolution of the polymer in a solvent.

As the polymer is suitable water soluble, water is also a microencapsulation vehicle.

Phase separator

As phase separator the following substances may be used:

a salt causing phase separation of the polymer in aqueous solution. Non-limiting examples are: sodium sulphate, ammonium sulphate, lithium sulphate, sodium citrate, sodium monobasic phosphate, sodium hexametaphosphate.

Posttreatment of microcapsules provided with HPMCP membrane

The microcapsules may be separated by filtering the microencapsulation medium and dried. If it is desired to obtain a more resistant, more impermeable and easier to dry membrane, microcapsules may be treated with solutions of membrane hardening acids. Non-limiting examples thereof are tartaric acid, citric acid, diluted hydrochloric acid.

Substances which may be microencapsulated

Microencapsulation can be carried out on all solid substances which are insoluble in the vehicle used for microencapsulation and in the solvents which are possibly used in the microencapsulation process. These substances must also be non reactive with the membrane and with the substances used in the microencapsulation process.

Non-limiting examples thereof are the following: ascorbic acid, acetyl-p-aminophenol, titanium dioxide, sodium chloride, potassium chloride, quinine and its salts, acetylsalicylic acid, nitrofurantoine, dihydroergotamine and its salts, dihydroergotoxine and its salts, vanillin, potassium penicillin, sodium dicloxacillin, anhydrous acidic ampicillin, trihydrated ampicillin, flucloxacillin, cloxacillin, cephalexine, bacampicillin, calcium salicilate, dextropropoxyphene chlorhydrate, pancreatin, trypsin, kymotrypsin, quinidine and its salts, dihydroquinidine and its salts, cimetidine, dipyridamole, icantone, allopurinol, ibuprofen.

Adjuvants for the microencapsulation process

The use of membrane hardening acids was already indicated hereinbefore. It is now to be mentioned the use of surfactants in the initial stage of microencapsulation. It was experimentally noted that the addition of little amounts of surfactants makes easier the deposition of the membrane around the cores.

Non-limiting examples of surfactants are sodium laurylsulphate, sodium dioctylsulphosuccinate, Tween, Span. The properties of the membrane such as plasticity, impermeability, may be improved inter alia by adding plasticizers for HPMCP. Non-limiting examples thereof are dibutylphthalate, triacetin, acetylated monoglycerides.

Additives which may be used in the final microencapsulation stage are absorbents or dehydratants; its use actually improves drying of microcapsules. Non-limiting examples thereof are syloid, aerosil, celkate, sodium sulphate. These substances may be added in any proportion even if they are generally comprised between 5% and 30% of the substance to be microencapsulated.

Gelatine-HPMCP membrane

If at the beginning of the microencapsulation process in an aqueous vehicle a gelatine solution is added, during the subsequent addition of phase separator, the simultaneous coacervation of both polymers is obtained, so that a deposition of a membrane of gelatine and HPMCP around the cores occurs. The concentration of the gelatine solution as well as the gelatine/HPMCP ratio may vary in a wide range, even if in the first case the concentration of gelatine is generally between 5 and 20% and in the second case the gelatine/HPMCP ratio is between 1:2 and 2:1, being generally 1:1.

Also in this case the membrane of the microcapsules may be subjected to a hardening treatment either by addition of diluted acids as hereinbefore mentioned, or by addition of aldehydes such as glutaraldehyde, or generally of substances adapted to react with the carboxy or amine groups of gelatin.

Microencapsulation process

According to the vehicle used it may be of the following types, it being understood that all percentages and ratios herein are by weight unless otherwise stated.

Aqueous microencapsulation process

HPMCP is dissolved in an amount between 1 and 20%, preferably 5%, in a solution of sodium bicarbonate in distilled water. Then the substance to be microencapsulated is dispersed in this solution by proper agitation. The ratio between substance and HPMCP may be in the range between 0.5:1 and 100:1, although it is generally comprised between 1:1 and 20:1. Always under agitation the phase separator is added and if necessary, temperature and pH value are varied. HPMCP separated in the form of liquid droplets coating the substance to be microencapsulated.

Deposition of the coacervate is fostered by adding a surfactant. The sequence of operations described so far may changed according to the requirements; thus it is for instance possible to disperse the substance to be microencapsulated in the solution of the phase separator and then the HPMCP solution is slowly added. The HPMCP solidifies by merely extending the agitation time, by adding an excess of phase separator, by cooling or by a combination of these factors.

The membrane may be further hardened by acidification of the dispersion. The microcapsules obtained may be separated by filtration and dried. Drying may be made easier by adding water absorbing substances.

The following examples are illustrative of some preparations carried out following the method of the present invention, and they shall not be construed as limiting in any way the scope of the invention.

EXAMPLE 1

(a) 3,800 ml of distilled or deionized water and 48 g of sodium bicarbonate are poured in a 5 l beaker. Under agitation 200 g of HPMCP grade HP 55 are added.

(b) 150 ml of the so obtained solution are placed in a 1,000 ml beaker.

(c) 2 ml of sodium laurylsulphate in a 5% aqueous solution and then 112,5 g of nitrofurantoine are added.

(d) 150 ml of a saturated solution of lithium sulphate are added dropwise, obtaining the phase separation of the HP 55 membrane which deposits around the nitrofurantoine crystals so as to form the microcapsules.

(e) 11 g of syloid are added. Microcapsules are filtered and dried.

EXAMPLE 2

The procedure of Example 1 is followed up to point (d) inclusive, then 10% citric acid is added until the pH value of the medium is brought to 4.2 and agitation is carried on for 15 minutes. Then agitation is stopped and it is left to clear. The supernatant liquid is removed and replaced by an equal amount of distilled water. The operation is repeated twice, then the nitrofurantoine microcapsules are separated by filtration and dried.

EXAMPLE 3

(a) 950 ml of distilled water and 12 g of sodium bicarbonate are poured in a 2 l beaker. 50 g of HPMCP grade HP 50 are added under agitation.

(b) 200 ml of the so obtained solution are placed in a 1.5 l beaker and diluted with 200 ml of distilled water.

(c) 0.3 ml of Tween 80 and 150 g of nitrofurantoine are added.

(d) 400 ml of a saturated solution of lithium sulphate are added dropwise in order to obtain a complete and continuous deposition of the polymer around the crystals of nitrofurantoine.

(e) 15 g of syloid are added and than the microcapsules are separated by filtration and dried.

EXAMPLE 4

The procedure of Example 3 is followed up to point (d) inclusive. Then a 10% solution of citric acid is added until the pH value of the medium is brought to 4.0 and agitation is carried on for 15 minutes.

Agitation is stopped and it is left to clear. The supernatant liquid is removed and replaced by an equal amount of distilled water. The operation is repeated twice, then microcapsules of nitrofurantoine are separated by filtration and dried.

EXAMPLE 5

140 ml of the HP 50 solution in water prepared according to Example 3 (a) are placed in a 400 ml beaker. Then 1 ml of a 1% water solution of dioctyl sodium sulphosuccinate and 35 g of dipyridamole are added. 140 g of a saturated solution of lithium sulphate are added dropwise is order to obtain the phase separation of the polymer which deposits around the dipyridamole crystals. The membrane of the microcapsules is then hardened bringing the pH value of the medium to 4.0 with tartaric acid. The so obtained microcapsules are washed three times with water, as described in Example 2, and then are filtered and dried.

EXAMPLE 6

In a 700 ml beaker there are sequentially added: 100 ml of a 5% aqueous solution with a pH value of 7.4 of HPMCP grade HP 55, 100 ml of distilled water, 1 ml of a 1% water solution of dioctyl sodium sulphosuccinate. Then 40 g of Hycantone are added under agitation and 250 ml of a 20% water solution of sodium sulphate are dripped slowly. The microcapsules obtained are filtered, mixed with 1 g of Aerosil and then dried.

The dried microcapsules are suspended in a 20% solution of paraffin in cyclohexane. Agitation is carried out for 15-30 minutes, then it is filtered and dried. In such a way the paraffin closes the pores of the membrane, so as to improve impermeability to gastric juices of the microcapsules.

EXAMPLE 7

400 ml of a 2.5% aqueous solution of HPMCP grade HP 50 are placed in a 1,200 ml beaker. 30 g of cimetidine are added and then 400 ml of a 20% water solution of sodium hexametaphosphate are dripped slowly. The obtained microcapsules are filtered, mixed with 1 g of Aerosil and then dried.

EXAMPLE 8

100 ml of a 5% solution of HPMCP grade HP 50 in deionized water are placed in a 400 ml beaker. 50 g of noscapine are added and then under agitation a 40% water solution of tribasic sodium citrate is added dropwise.

To make easier the deposition of the coacervate around the noscapine crystals, 1 cc of a 1% solution of sodium dioctylsulphosuccinate is added. The obtained microcapsules are filtered, mixed with 2 g of Celkate and dried.

EXAMPLE 9

In a beaker the following substances are added under agitation while the temperature is kept constant around 50° C.: 100 ml of a 5% water solution of HPMCP grade HP 50 prepared as described in Example 3 and heated to 50° C.; 50 ml of a 10% water solution of gelatine having a pH value of 6.0 and a temperature of 50° C.; 150 g of nitrofurantoine.

The mixture is always kept at 50° C. and under agitation, and 150 ml of a saturated water solution of lithium sulphate are added slowly. The simultaneous deposition of gelatine and HPMCP is thus obtained around the particles of nitrofurantoine. At this point the microcapsules may be separated by filtration and dried or the membrane may be hardened by adding glutaraldehyde. More particularly, in this example the pH value of the mixture was first brought to 6 by adding few drops of a 10% solution of sulphuric acid and then 2 ml of a 25% solution of glutaraldehyde were added.

After stirring for 12 hours, microcapsules are washed three times with 200 ml of distilled water and then separeted by filtration and dried in a fluidized bed.

EXAMPLE 10

The release rate of the active ingredient from the microcapsules with HPMCP was determined with the method of the rotary bottle (RBM), slightly modified. The data found for the samples described in Example 1, 2, 3 and 4 are hereinafter set forth.

|  | HP 50 | | HP 55 | |
| --- | --- | --- | --- | --- |
| Release in juice | 1 | 2 | 3 | 4 |
| 1 h pH 1.5 | 21.5% | 19.2% | 27.9% | 29.3% |
| 2 h pH 4.5 | 37.1% | 31.9% | 42.3% | 44.9% |
| 4 h pH 6.9 | 105.1% | 72.1% | 84.4% | 91.0% |

In the same samples time and pH value of the microcapsule membrane dissolution were observed at the microscope. After 1 hour at pH 1.5 the membrane is intact. After another hour at pH 4.5 the membrane is still intact. After 2 further hours at pH 6.9 on the contrary the membrane is totally dissolved.

It is to be understood that several modifications, variations, additions and substitutions may be resorted to the various stages and the various elements comprising the method according to the present invention, without departing however from its spirit or its scope, as defined in the appended claims.

I claim:

1. A process for preparing microcapsules in a liquid vehicle, comprising the following steps:
   (1) dissolution of a membrane-forming cellulosic polymer in a solvent which is the microencapsulation vehicle;
   (2) addition of cores of a substance to be microencapsulated to said solution;
   (3) formation of a coacervate by adding a substance adapted to cause phase separation;
   (4) deposition of the coacervate, forming a continuous coating of polymer around the cores of the substance; and
   (5) solidification of the polymer;
the improvement comprising the fact that the membrane-forming cellulosic polymer is a cellulose phthalate having the following chemical structure:

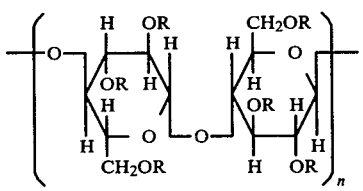

wherein R is hydrogen or a methyl, hydroxypropyl, carboxybenzoyl, 2-(2-carboxybenzoyl)propyl, or acetyl group, at least one R being always carboxybenzoyl, that the polymer is dissolved in aqueous or buffer solution, and that the phase separator is a substance causing phase separation of the cellulose phthalate from aqueous solution at a pH $\geq$ 5.

2. A process according to claim 1, wherein the polymer forming the membrane of the microcapsules is hydroxypropylmethylcellulose phthalate (HPMCP).

3. A process according to claims 1 or 2, wherein another polymer is present in the membrane.

4. A process according to claim 1 or 2, wherein a plasticizer is present in the membrane.

5. A process according to claim 1 or 2, wherein the microencapsulation vehicle is an aqueous solution or a buffer solution having a pH $\geq$ 5.

6. A process according to claim 1 or 2, wherein the ratio between the substance to be microencapsulated and membrane is between 0.5:1 and 100:1.

7. A process according to claim 1 or 2, wherein microencapsulation is fostered by adding a surfactant.

8. A process according to claim 1 or 2, wherein the membrane of the microcapsules is reacted with material adapted to harden the membrane at a pH value less than 5.

9. A process according to claim 1 or 2, wherein drying of microcapsules is fostered by adding a substance adapted to absorb water and dehydrate the membrane.

10. A process according to claim 1 or 2, wherein the membrane of the microcapsules is made impermeable by means of a post treatment with a wax.

11. A process of claim 9, wherein the added substance is a silicium dioxide or silicate.

12. A process of claim 8, wherein the material is an acid.

13. A pharmaceutical substance microencapsulated with a membrane-forming cellulose phthalate polymer by coacervation from an aqueous vehicle produced by the procedure of claim 1.

14. A process of claim 2, wherein gelatine is also present in the membrane.

15. A process of claim 12, wherein gelatine is also present in the membrane and wherein aldehyde is added.

16. A process according to claim 1 or 2, wherein the ratio between the substance to be microencapsulated and the membrane is between 1:1 and 20:1.

* * * * *

UNITED STATES PATENT AND TRADEMARK OFFICE
CERTIFICATE OF CORRECTION

PATENT NO. : 4,460,563
DATED : July 17, 1984
INVENTOR(S) : Massimo Calanchi

It is certified that error appears in the above—identified patent and that said Letters Patent is hereby corrected as shown below:

Col. 3, lines 5 & 6; the sentence "As the polymer is suitable water soluble, water is also a microencapsulation vehicle." should read -- As the polymer is also water soluble, water is a suitable microencapsulation vehicle. --

Col. 5, line 49; "is" should read -- in --

Col. 6, lines 46 & 47; "separeted" should read -- separated --

Col. 8, line 4; "claims" should read -- claim --

Signed and Sealed this

Ninth Day of April 1985

[SEAL]

Attest:

DONALD J. QUIGG

Attesting Officer  Acting Commissioner of Patents and Trademarks